United States Patent [19]
Karimian et al.

[11] Patent Number: 6,060,472
[45] Date of Patent: *May 9, 2000

[54] THIADIAZOLE COMPOUNDS USEFUL AS INHIBITORS OF $H^+/K^+$ ATPASE

[75] Inventors: Khashayar Karimian, Mississauga; Tim Fat Tam, Woodbridge; Regis C. S. H. Leung-Toung, Mississauga; Wanren Li, Etobicoke, all of Canada

[73] Assignee: Apotex Inc., Weston, Canada

[ * ] Notice: This patent issued on a continued prosecution application filed under 37 CFR 1.53(d), and is subject to the twenty year patent term provisions of 35 U.S.C. 154(a)(2).

[21] Appl. No.: 09/055,209

[22] Filed: Apr. 6, 1998

[51] Int. Cl.$^7$ ...... A61K 31/496; C07D 417/04; C07D 417/14
[52] U.S. Cl. ...... 514/252; 544/357; 544/364; 544/367
[58] Field of Search ...... 544/364, 357, 544/367; 514/252

[56] References Cited

U.S. PATENT DOCUMENTS 4,613,601 9/1986 Regnier et al. ...... 514/252

*Primary Examiner*—Emily Bernhardt
*Attorney, Agent, or Firm*—Nixon & Vanderhye P.C.

[57] ABSTRACT

Novel 3,5-disubstituted 1,2,4-thiadiazole compounds are provided, which are effective in treating peptic ulcers by the inhibition of $H^+/K^+$-ATPase. The compounds of the present invention are 3,5-disubstituted 1,2,4-thiadiazole corresponding to the general formula (I):

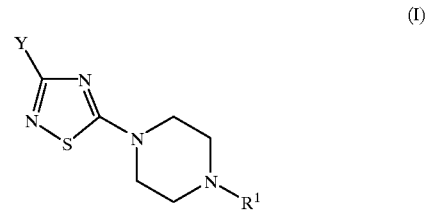

where $R^1$ is a group with cell penetration properties for the inhibition of the enzyme in-vitro and in-vivo, and Y is a substituent that tunes the reactivity of the inhibitor towards the cysteine residue of $H^+/K^+$-ATPase. The Y group may also serve in recognition.

21 Claims, 2 Drawing Sheets

THIADIAZOLE COMPOUNDS USEFUL AS INHIBITORS OF H+/K+ ATPASE

FIELD OF THE INVENTION

This invention relates to (i) novel 5-amino-1,2,4-thiadiazoles and the pharmaceutically acceptable acid addition salts and base addition salts thereof, (ii) the use of these compounds as inhibitors of proton pump H+/K+-ATPase (iii) pharmaceutical compositions comprising a compound of this invention and at least one pharmaceutical excipient; and (iv) processes for preparing the compounds of this invention.

BACKGROUND OF THE INVENTION AND PRIOR ART

The compounds of this invention are 5-amino substituted derivative of 1,2,4-thiadiazoles having the following structure:

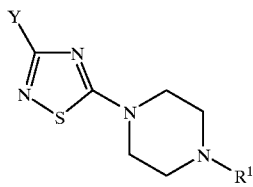

The invention also relates to the use of certain of these thiadiazoles as inhibitors of H+/K+-ATPase and agents for the treatment of peptic ulcer.

A class of 1,2,4-thiadiazole compounds with a piperazinyl substituent at the C-5 are disclosed in U.S. Pat. Nos. 4,352,808, 4,177,272, 4,629,728, 4,629,728, and 5,478,939 as having pharmaceutical application in treating central cholingeric disfunction, disorder connected with hypoxemia, microbial infection and Parkinson's disease. U.S. Pat. No. 5,405,853 discloses a class of 1,2,4-thiadiazoles with a non-aromatic azacyclic ring at the C-5 position and claims its use in the treatment of senile dementia. U.S. Pat. No. 4,242,350 teaches 5-guanidino derivative of 1,2,4-thiadiazole as histamine H-2 receptor antagonist useful in the inhibition of acid secretion. However, these compounds are not 5-piperazinyl-1,2,4-thiadiazoles.

Peptic ulcers are one of the most prevalent diseases in industrialized nations. Control of gastric acid secretion is the main therapy for peptic ulcers. Acid secretion is in turn brought about by the interaction of three physiological stimulants, gastrin, acetylcholine and histamine with their respective parietal cell receptors. Prior to the discovery of histamine $H_2$-receptor antagonists such as cimetidine and ranitidine, peptic ulcer treatment consisted of antacid therapy and anticholinergic drugs (eg. dicyclomine HCl). However, with the advent of $H_2$-receptor antagonists, treatment with anticholinergic agents has been largely supplanted by histamine $H_2$-receptor antagonist therapy. The development of this class of therapeutic entities presents one of the most important advances in the field of medicinal chemistry.

Another major development in the treatment of peptic ulcers has been realized with the introduction of H+/K+ ATPase inhibitors e.g. omeprazole. The enzyme H+/K+ ATPase, which is also known as the proton pump, is located in the membrane of gastric parietal cells and is responsible for the transport of protons from blood to lumen, which in turn results in decreasing the pH of stomach contents which leads to aggravation of peptic ulcers.

Therefore, the inhibition of this enzyme is one of the primary basis of treatment of peptic ulcer in humans. Thiol trapping agents can be used to inhibit the enzyme H+/K+-ATPase. An example of such compound is omeprazole.

Omeprazole itself is in fact a prodrug which under acidic conditions converts to the active drug, namely its corresponding sulfenamide. The mechanism of action of omeprazole is well-studied and is known to involve a nucleophilic attack of one (or two) thiol group(s) of the H+/K+-ATPase on the sulfur atom of the chemically active sulfenamide. The resulting chemical modification of the thiol group (s) of the enzyme (formation of a disulfide bond between the H+/K+-ATPase sulfur and the sulfur of the benzimidazole pyridinium salt) causes the observed inhibition of the proton pump. The complex cascade of molecular events that lead to the inhibition of the H+/K+ ATPase is shown in FIG. 1.

As shown in FIG. 1, the presence of acid is a prerequisite to the conversion of omeprazole to its chemically active sulfenamide. However, the resulting sulfenamide is a labile molecule which transforms further to a number of other compounds that are unreactive to nucleophilic attack by the H+/K+-ATPase thiol(s) and are therefore incapable of inhibiting the enzyme. These transformations are acid catalyzed. Accordingly, in a strict chemical sense, while acid is a prerequisite for the conversion of omeprazole to its active form, it also acts to its detriment. As a partial solution to this problem, omeprazole drug products are formulated to resist the acidic medium of the stomach by enteric coating. The coating is dissolved in the relatively neutral environment of the duodenum and omeprazole is absorbed into the blood stream which carries the prodrug to the proton pump. It should be emphasized however, that the conversion of the prodrug to the active enzyme inhibitor can only be achieved in acidic media which also results in substantial degradation of the active sulfenamide. In summary, the instability of omeprazole in acidic environments, which is a prerequisite to its activation into a proton pump inhibitor, is the major shortcoming of this drug.

Acid instability of omeprazole not only decreases the bioavailability of the drug, but also creates considerable difficulty in its formulation, adding to the cost of the final drug product. These inherent problems are also observed in the large number of omeprazole analogues that have been synthesized to increase the acid stability of their corresponding sulfenamide. Two factors contribute to the instability of omeprazole in acidic media. First, as observed with other sulfoxides, omeprazole undergoes a characteristic acid catalyzed degradation known as the Pummerer rearrangement. Second, protonation of the trivalent nitrogen of sulfenamide followed by nucleophilic attack on the sulfur atom is another characteristic reaction of these compounds. Enzyme inhibition is observed only when the H+/K+-ATPase-S- acts as the nucleophile. On the other hand, sulfenamide degradation is caused when Cl acts as the nucleophile. Accordingly, any slight gain in acid stability of the sulfenamide (or sulfoxide) that may be introduced by chemical modification (resistance to Cl attack) is offset by a decrease in reactivity of the analogue to H+/K+-ATPase-S- attack. The net result is a less effective drug.

Another shortcoming of omeprazole is its variability of action in different patients. There is clinical evidence of a variable response to omeprazole as determined by inhibition of gastric acid release in peptic ulcer patients, attributable to a high first pass effect for the biotransformation of omeprazole, and the fact that the metabolism of omeprazole appears to be under polymorphic genetic control, resulting in variable amounts of drug reaching the systemic circulation following a given dose.

In view of the above, shortcomings of omeprazole and its related analogues (pantroprazole, lansoprazole) as irreversible proton pump inhibitors, other research groups have embarked in the development of reversible potassium competitive inhibitors of gastric H$^+$/K$^+$ ATPase. The irreversible inhibitor like omeprazole reacts with the cysteine residue on the enzyme to form a disulfide bond, while the reversible potassium competitive inhibitors do not react with the enzyme to form any type of covalent bond. Reversible inhibition is a result of binding of the inhibitor to the enzyme (Physiological Reviews, 1995, 75, 155). Quinoline derivatives are reported as highly effective reversible inhibitors of gastric acid secretion in animals (J. Med. Chem., 1992, 35, 1845–1852; J. Med. Chem., 1992, 35, 3418–3422; J. Med. Chem., 1990, 33, 527–533), but these compounds have short life inhibitory effect and have not been developed as clinically useful anti-secretory agents. Therefore, there is a need for a new generation of proton pump inhibitors which are acid stable. U.S. Pat. No. 5,677,302 discloses bicyclic and tricyclic imidazo[1,2-d]-thiadiazole derivatives as proton pump inhibitors. Compounds of the present invention are structurally different, the compounds are monocyclic 1,2,4-thiadiazoles with a single unfused five membered 1,2,4-thiadiazole ring.

SUMMARY OF INVENTION

It is an object of the present invention to provide novel pharmaceutical compounds, and compositions containing them, which are active as H$^+$/K$^+$-ATPase inhibitors, and hence useful in the treatment of peptic ulcers in mammals.

It is a further object of the invention to provide methods for the synthesis of such compounds.

The present invention is based upon the discovery of a class of novel chemical compounds that are effective as H$^+$/K$^+$-ATPase inhibitors and that are also acid stable.

The new chemical compounds of the invention are characterized by having a 4-R$^1$-substituted piperazinyl group at the C5 position of 1,2,4-thiadiazole, a recognition group R$^1$ with cell penetration properties through the adjustment of the lipophilicity and pKa of the compound and by having at the C3 position of 1,2,4-thiadiazole a group which tunes the reactivity of the compound.

Thus, according to the present invention, there are provided various 3,5 disubstituted 1,2,4-thiadiazole compounds corresponding to the general formula (I):

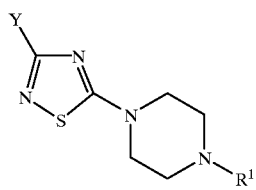

(I)

or pharmaceutically acceptable salts thereof, wherein:
R$^1$ is selected from:
(1) 2-pyrazinyl, 2-pyridyl, 3-pyridyl, 4-pyridyl wherein the pyridyl ring is optionally substituted with amino, alkyl, halogen, hydroxy, alkoxy, alkoxycarbonyl or carboxy;
(2) a group of formula:

—CHR$^2$R$^3$ in which R$^2$ and R$^3$ are independently carboalkoxy, carboxamido, alkanoyl, aryl or heterocyclyl, the aryl or heterocyclyl ring being optionally substituted with amino, halo, dialkylamino, hydroxy, alkoxy or alkyl;

Y is selected from:
(1) lower alkoxy, lower cycloalkyoxy, lower arylalkoxy, heterocyclyloxy, lower heterocyclylalkoxy, the alkyl or aromatic ring being optionally substituted with 1 to 2 substituents selected from amino, alkoxy, hydroxy, halo, alkylamino or dialkylamino;
(2) lower alkyl, lower cycloalkyl, lower heterocyclylalkyl, heterocyclyl, aryl, lower arylalkyl, lower arylalkenyl, lower heterocyclylalkenyl, the alkyl or aromatic ring being optionally substituted with 1 to 2 substituents selected from amino, alkoxy, hydroxy, halo, alkylamino or dialkylamino;
(3) lower alkoxycarbonyl or carbonyl;
(4) ketone of formula:

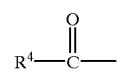

wherein R$^4$ is lower alkyl, lower cycloalkyl, lower heterocyclylalkyl, aryl or lower arylalkyl, the alkyl or aromatic ring being optionally substituted with 1 to 2 substituents selected from amino, alkoxy, hydroxy, halo, alkylamino or dialkylamino;
(5) carbamoyl group of formula

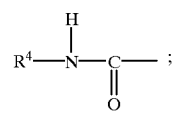

with R$^4$ being as defined above;
(6) amino, lower alkylamino, lower dialkylamino,
(7) amide of formula:

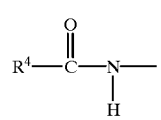

with R$^4$ being as defined above;
(8) alcohol of formula:

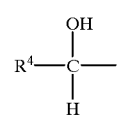

with R$^4$ being as defined above;
(9) sulfone of formula:

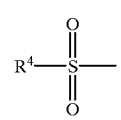

with R$^4$ being as defined above;

(10) sulfoxide of formula:

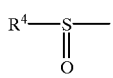

with R⁴ being as defined above;
(11) sulfonamide of formula:

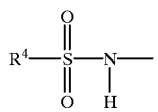

with R⁴ being as defined above;
(12) lower alkylthio, lower arylalkylthio, arylthio;
(13)

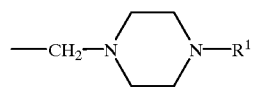

with R¹ being as defined above.

BRIEF REFERENCE TO THE DRAWINGS

DESCRIPTION OF PREFERRED EMBODIMENTS

Preferred compounds of formula (I) according to the invention are those in which R¹ is 2-pyridyl or 1-(4-chlorophenyl)-1-phenylmethyl.

Particularly preferred compounds of formula (I) are those in which Y is 3-methyl, 3-phenyl, 3-methoxy, 3-benzoyl, Ph—CH(OH)—, 1-(3-chlorophenyl)-1-(hydroxy) methyl, 3-chlorobenzoyl, 2-pyridylacetyl, 1-hydroxy-1-phenylmethyl, or 4-pyridin-2-yl-piperazin-1-yl)-methyl; and R¹ is 2-pyridyl.

Also particularly preferred compounds of formula (I) are those in which Y is 1-hydroxy-1-phenylmethyl or benzoyl and R¹ is 1-(4-chlorophenyl)-1-phenyl-methyl or 2-pyridyl.

Most preferred compounds of formula (I) are: 3-phenyl-5-{4-[pyridin-2-yl]-piperazin-1-yl}-1,2,4-thiadiazole 3-benzoyl-5-{4-[pyridin-2-yl]-piperazin-1-yl}-1,2,4-thiadiazole 3-chlorobenzoyl-5-{4-[pyridin-2-yl]-piperazin-1-yl}-1,2,4-thiadiazole The preferred compounds according to the invention have good cell penetration properties and are acid stables.

Figure 1:
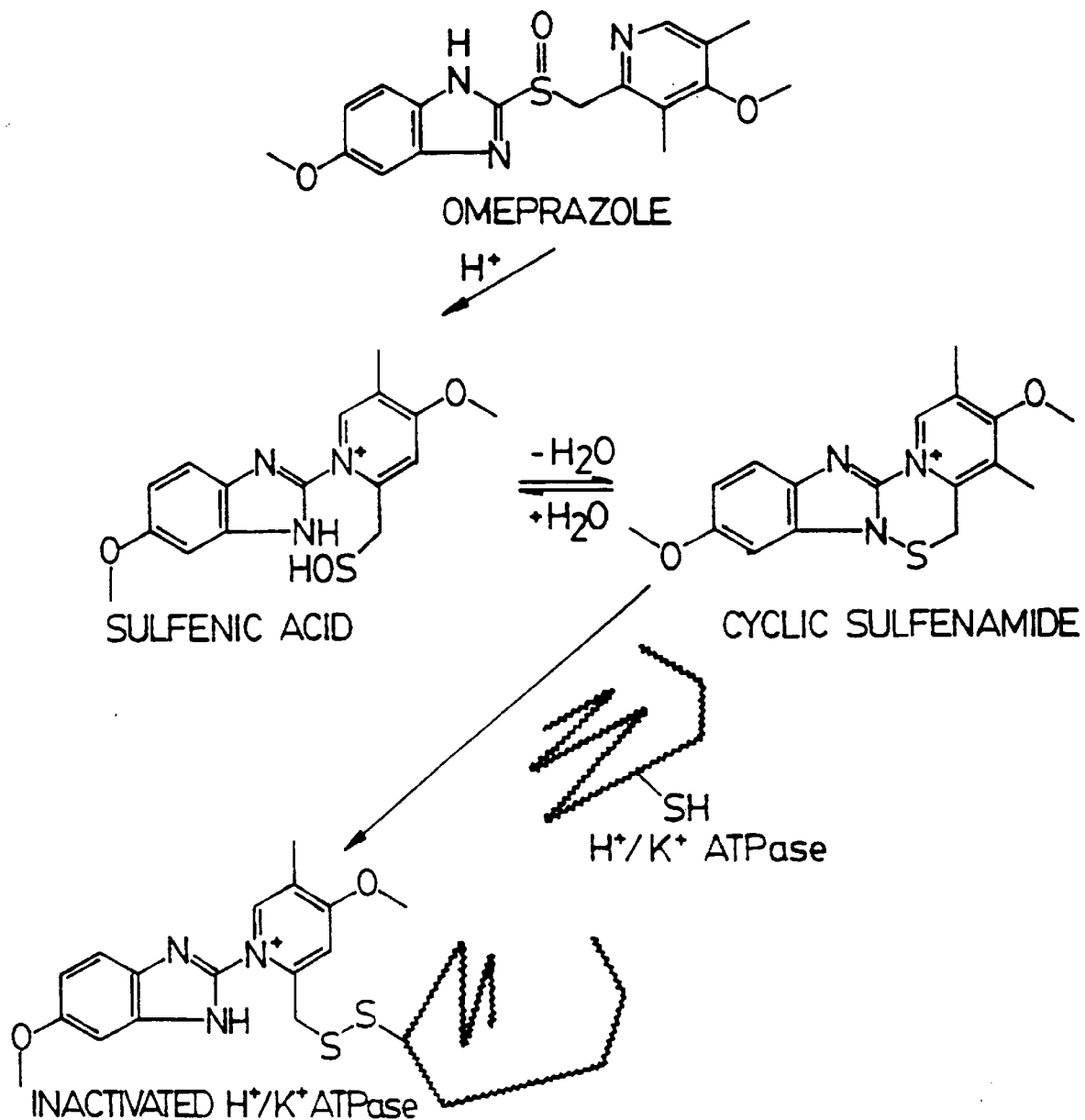
FIG. 1 is a diagrammatic representation of the mode of chemical interaction of omeprazole and H⁺/K⁺-ATPase.
Figure 2:
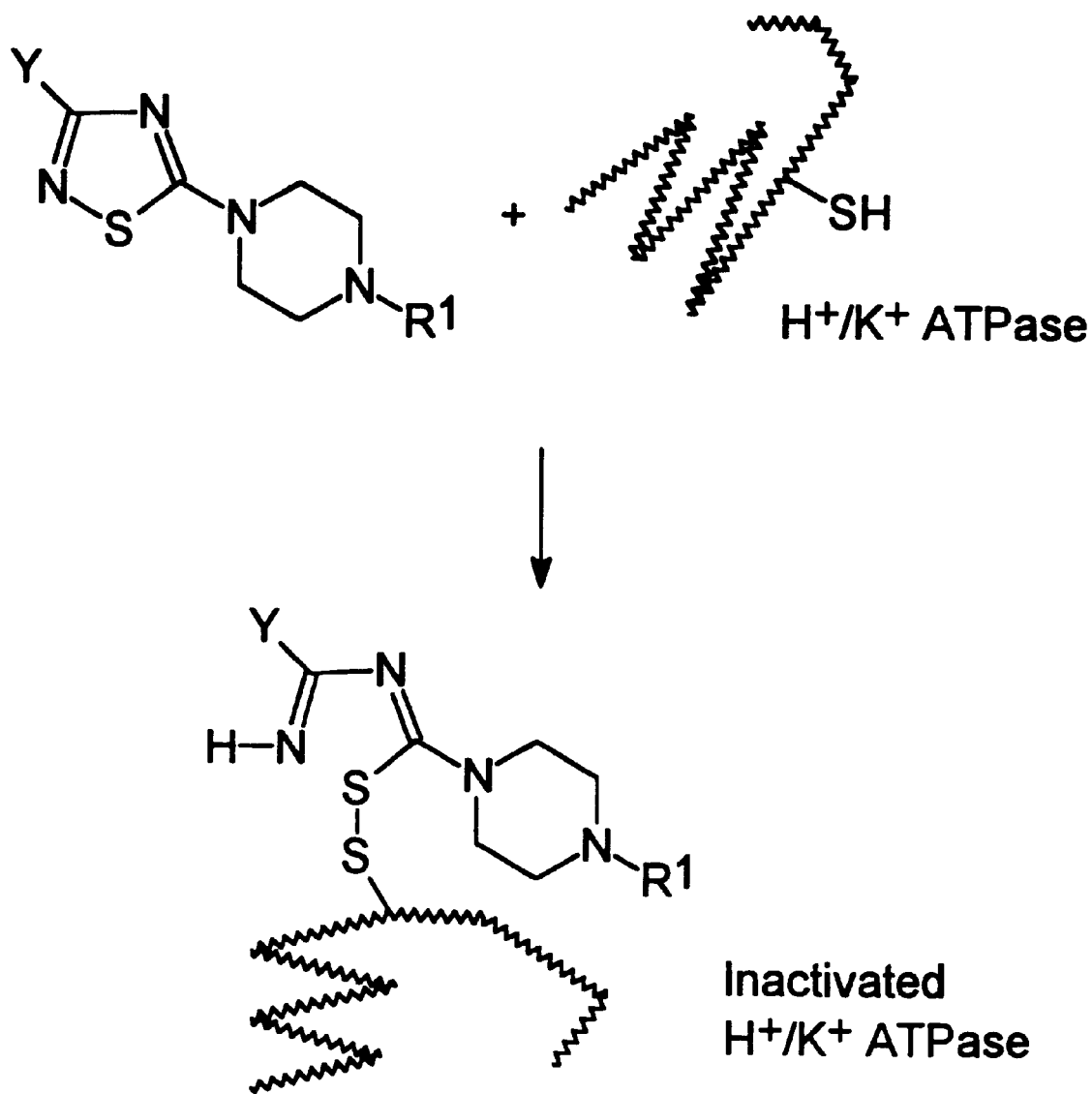
FIG. 2 is a diagrammatic representation of a proposed chemical interactions of compounds according to the invention with H⁺/K⁺-ATPase and with cysteine of the enzyme.

While it is not intended that the present invention should be limited to any particular theory or mode of action, it is believed that the compounds of the present invention interact to inhibit the action of the proton pump enzyme, by reacting with sulfhydryl groups on surface cysteine residues of the enzyme. This is generally illustrated in FIG. 2 of the accompanying drawings. The S—N bond in 1,2,4-thiadiazoles has a high energy content which originates, at least in part, from non-bonded electron repulsion between sulfur atom d orbitals and nitrogen atom p orbitals. 1,2,4-Thiazoles are therefore likely to be susceptible to nucleophilic attack. It has been reported over forty years ago that 1,2,4-thiadiazoles undergo S—N bond cleavage with reducing agents (Gordeler, Chem. Ber., 1954, 87, 57). The thiol groups of H⁺/K⁺-ATPase appear to act as reducing agents (nucleophiles), thereby become chemically modified as shown in FIG. 2, with resulting inhibition of the enzymatic activity. Group Y at the 3-position of the thiadiazole nucleus, because of its electron withdrawing nature, activates the adjacent bonds to facilitate this reaction.

As used herein:

The term "lower", as applied for example to lower alkyl, means 1 to 8 carbon atoms.

The term "aryl", alone or in combination, means a phenyl or naphthyl radical which optionally carries one or more substituents selected from alkyl, alkoxy, halogen, hydroxy, amino and the like, such as phenyl, p-tolyl, 4-methoxyphenyl, 4-(tert-butoxy)phenyl, 4-fluorophenyl, 4-chlorophenyl, 4-hydroxyphenyl, 1-naphthyl, 2-naphthyl and the like.

The term "arylalkoxy carbonyl", alone or in combination, means a radical of the formula —C(O)—O-arylalkyl, in which the term "arylalkyl" has the significance given above. An example of an arylalkoxy-carbonyl radical is benzyloxycarbonyl.

The term "arylalkyl" means an alkyl radical in which one hydrogen atom is replaced by an aryl radical, such as benzyl, phenylethyl and the like The term "arylalkenyl" means an alkenyl radical in which one hydrogen atom is replaced by an aryl radical such as 3-phenylallyl, 2-phenylallyl, 1-phenylallyl and the like.

The term "cycloalkylcarbonyl" means an acyl group derived from a monocyclic or bridged cycloalkanecarboxylic acid such as cyclopropanecarbonyl, cyclohexanecarbonyl, adamantanecarbonyl, and the like, or from a benz-fused monocyclic cycloalkanecarboxylic acid which is optionally substituted by, for example, alkylamino, such as 1,2,3,4-tetrahydro-2-naphthoyl, 2-acetamido-1,2,3, 4-tetrahydro-2-naphthoyl.

The term "arylalkanoyl" means an acyl radical derived from an aryl-substituted alkanecarboxylic acid such as phenylacetyl, 3-phenylpropionyl, hydrocinnamoyl, 4-phenylbutyryl, (2-naphthyl)acetyl, 4-chlorohydrocinnamoyl, 4-aminohydro-cinnamoyl, 4-methoxyhydrocinnamoyl, and the like.

The term "aroyl" means an acyl radical derived from an aromatic carboxylic acid. Examples of such radicals include aromatic carboxylic acid, an optionally substituted benzoic or naphthoic acids such as benzoyl, 4-chloro-benzoyl, 4-carboxybenzoyl, 4-[(benzyloxy-carbonyl] benzoyl, 1-naphthoyl, 2-naphthoyl, 6-carboxy-2-naphthoyl, 6-[(benzyloxy)carbonyl]-2-naphthoyl, 3-benzyloxy-2-naphthoyl, 3-hydroxy-2-naphthoyl, 3-[(benzyloxy) formamido]-2-naphthoyl, and the like.

The term "heterocyclyl", as used herein except where noted, represents a stable 5- to 7-membered mono or bicyclic or stable 7- to 10-membered bicyclic heterocyclic ring which is either saturated or unsaturated, and which consists of carbon atoms, and from one to three heteroatoms selected from the group consisting of N, O, S, and wherein the nitrogen and sulfur heteroatoms may be optionally oxidized, and the nitrogen atom may optionally be quaternized, and including any bicyclic group in which any of the above defined heterocyclic rings is fused to a benzene ring. The heterocyclic ring may be attached at any heteroatom or carbon atom which results in the creation of a stable structure. Examples of such heterocyclic elements, commonly known as heterocyclyl include piperidinyl, piperazinyl, 2-oxopiperazinyl, 2-oxopiper-azinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolidinyl, isoxazolyl, isoxazolidinyl, morpholinyl, thiazolyl, thiazolidinyl, isothiazolyl, quinuclidinyl, isothiazoli-dinyl, indolyl, quinolinyl, isoquinolinyl, benzimidazolyl, thiadiazolyl, benzopyranyl, benzothiazolyl, benzoxazolyl, furyl, tetrahydrofuryl, tetrahydropyranyl, thienyl, benzothienyl, tetrahydroquinolinyl (e.g. 1,2,3,4-tetrahydro-2-quinolinyl, etc.), 1,2,3,4-tetrahydro-isoquinolinyl (e.g. 1,2,3,4-tetrahydro-1-oxo-isoquinolinyl etc.), quinoxalinyl, beta-carbolinyl, 2-benzofurancarbonyl, thiamorpholinyl, thiamorpholinyl sulfoxide, thiamorpholinyl sulfone, oxadiazolyl and the like. The heterocycle may be substituted on one or more carbon atoms or heteroatom which results in the creation of a stable structure.

The term "aryloxyalkanoyl" means an acyl radical of the formula aryl-O-alkanoyl and the term "heterocyclyloxycarbonyl" means an acyl group derived from heterocyclyl-O—CO— wherein heterocyclyl is defined above.

The term "heterocyclylalkanoyl" means an acyl radical derived from a heterocyclyl-substituted alkane carboxylic acid wherein heterocyclyl has the same meaning given above.

The term "heterocyclylalkoxycarbonyl" means an acyl radical derived from a heterocyclyl-substituted alkyl-O-COOH wherein heterocyclyl has the same significance given above.

The term "aminoalkanoyl" means an acyl radical derived from an amino-substituted alkanecarboxylic acid wherein the amino group can be a primary, secondary or tertiary amino group containing substituents selected from hydrogen, and alkyl, aryl, arylalkyl, cycloalkyl, cycloalkylalkyl radicals and the like.

"Optional" or "optionally" means that the subsequently described event or circumstances may or may not occur, and that the description includes instances where the said event or circumstance occurs and instances in which it does not. For example, "phenyl . . . optionally substituted" means that the phenyl may or may not be substituted and that the description includes both unsubstituted phenyl and phenyl wherein there is substitution.

Certain of the compounds of the invention have chiral centers and exist as optical antipodes. The invention described and claimed herein includes each of the individual enantiomers as well as their racemic modifications and the racemic mixture.

"Pharmaceutically acceptable, non-toxic salts" refers to pharmaceutically acceptable salts of the compounds of this invention which retain the biological activity of the parent compounds and are not biologically or otherwise undesirable (e.g. the salts are stable). Salts of the two types may be formed from the compounds of this invention: (1) Salts of inorganic and organic bases from compounds of formula I which have a carboxylic acid functional group. (2) Acid addition salts may be formed at the amine functional group of many of the compounds of this invention.

Pharmaceutically acceptable salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Pharmaceutically acceptable, non-toxic salts derived from organic bases include salts of primary, secondary and tertiary amines, substituted amines including naturally occurring substituted amines, cyclic amines and basic ion exchange resins. Such salts are exemplified by, for example, isopropylamine, trimethylamine, diethylamine, triethylamine, tripropylamine, ethanolamine, 2-dimethylaminoethanol, tromethamine, dicyclohexamine, lysine, arginine, histidine, caffeine, procaine, hydrabramine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, piperidine, tromethamine, dicyclohexylamine, choline and caffeine.

Pharmaceutically acceptable acid addition salts are formed with inorganic acids such as halo acids, sulfuric acid, nitric acid, phosphoric acid and the like and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The term "animals" refers to humans as well as all other animal species, particularly mammals (e.g. dogs, cats, horses, cattle, pigs etc.), reptiles, fish, insects and helminths.

The present invention provides synthetic methods for preparing compounds claimed in this invention. The choice of method depends largely upon the desired Y group, i.e. the substituent on C3 position in the final product.

In the first process, a compound of the present invention formula (I) is prepared by reaction of an amine of formula (II) with a piperazine derivative ZH. Examples of those amines are 2-pyridylpiperazine and 1-(3-chlorophenyl)-1-phenylmethylpiperazine. This method is appropriate for compounds in which Y is lower alkyl, lower alkoxy, heterocyclyl, 1-haloalkyl, aryl, dialkylamino.

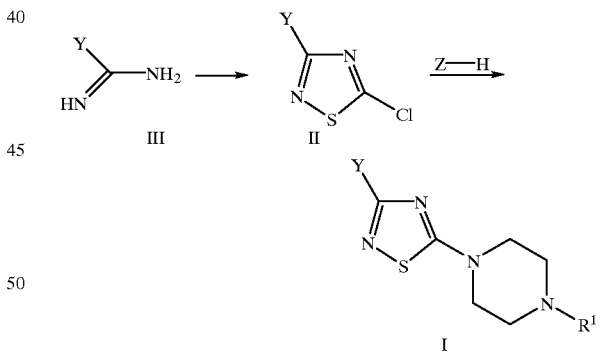

The reaction is normally carried out in an inert solvent such as N,N-dimethylformamide, tetrahydrofuran, dichloromethane, acetonitrile, dimethylsulfoxide in the presence or absence of a base such as 1 to 3 mole of triethylamine per mole of compound (II). These solvents may be used singly or in combination of any ratio as necessary. Reaction temperature can be chosen over the range of from 0° C. to 150° C., being preferrably about 10 to 65° C. Reaction time is normally about 1 to 50 hours, preferably 1 to 8 hours. The amount of amine used is 1 to 3 mole per mole of compound (II).

A compound of formula II can be produced by treating the corresponding amidine derivative IIII with perchloromethyl mercaptan in a two phase mixture of dichloromethane and sodium hydroxide at 0 to 25° C. for 2 to 6 hours.

Compound III used for these production methods can be prepared according to the following representative literature methods: U.S. Pat. No. 3,324,141; J. Org. Chem., 1962, 27, 2589; Chem. Ber., 1957, 90, 182.

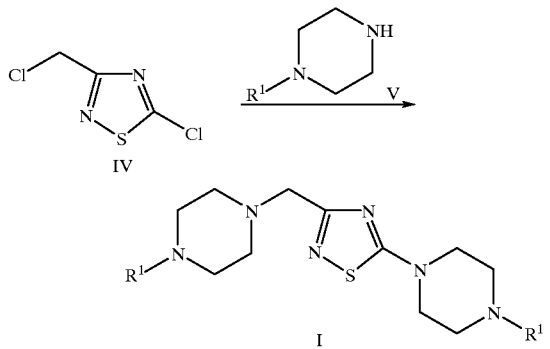

A second process for the preparation of compounds of formula I involves the use of the bis-chloro derivative IV as a starting material. The amines V reacts with compound IV in the presence of a phase transfer catalyst such as tetra-N-butylammonium bromide in an inert solvent such as dimethylformamide at room temperature over a period of 20 to 30 hours to give compound 1. This reaction is temperature dependent. At elevated temperature, preferably 70–90° C., the disubstituted product compound I is formed. This process is applicable to the preparation of 1,2,4-thiadiazole in which Y is a piperazinylmethyl group.

Certain compounds of this invention may be converted to their corresponding pharmaceutically acceptable acid addition salts by virtue of the presence of a basic amine nitrogen. These compounds may be converted from the free base form to various acid addition salts by treating with a stoichiometric excess of the appropriate organic or inorganic acid, such as, for example, phosphoric, pyruvic, hydrochloric or sulfuric acid and the like. Typically, the free base is dissolved in a polar organic solvent such as p-dioxane or dimethoxyethane, and the acid added thereto. The temperature is maintained between about 0° C. and 50° C. The resulting acid addition salt precipitates spontaneously or may be precipitated out of solution with a less polar solvent. These acid addition salts may be decomposed to the corresponding free base by treating with a stoichiometric amount of a suitable base, such as potassium carbonate or sodium hydroxide, typically in the presence of aqueous solvent, and at a temperature of between about 0° C. and 50° C. The free base form is isolated by conventional means, such as extraction with an organic solvent. Acid addition salts of the compounds of the present invention may be interchanged by taking advantage of differential solubilities of the salts, volatilities or acidities of the acids, or by treating with an appropriately loaded ion exchange resin. For example, the interchange is effected by the reaction of a salt of the compounds of formula I with a slight stoichiometric excess of an acid of a lower pKa than the acid component of the starting salt. This is carried out at a temperature between about 0° C. and the boiling point of the solvent being used.

For the treatment of peptic ulcers, the compounds of the present invention may be used orally, or parenterally in formulations containing conventional non-toxic pharmaceutically acceptable carriers, adjuvants and vehicles. The term parenteral as used herein includes subcutaneous injection or infusion techniques. In addition to the treatment of warm-blooded animals such as mice, rats, horses, cattle, sheep, dogs, cats, etc., the compounds of the invention are effective in the treatment of humans.

For compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as liquid pharmaceutically administrable compositions can, for example, be prepared by mixing, dissolving, dispersing, etc. the active compound as defined above and optional pharmaceutically adjuvants in a carrier, such as, for example, water, saline, aqueous dextrose, glycerol, ethanol, and the like, to thereby form a solution or suspension. If desired, the pharmaceutical composition to be administered may also contain a minor amount of non-toxic auxiliary substances such as wetting or emulsifying agents and the like, for example, sodium acetate, sorbitan monolaurate, triethanolamine sodium acetate, triethanolamine oleate, etc. Actual methods of preparing such dosage forms are known, or will be apparent to those skilled in this art: for example, see Remington's Pharmaceutical Sciences, Mack Publishing Company, Easton, Pa., 15th Edition, 1975. The composition of formulation to be administered will, in any event, contain a quantity of the active compounds in an amount effective to alleviate the symptoms of the subject being treated.

The pharmaceutical compositions containing the active ingredient may be in a form suitable for oral use, for example, as tablets, troches, lozenges, aqueous or oily suspensions, dispersible powders or granules, emulsions, hard and soft capsules, or syrups or elixirs. Compositions intended for oral use may be prepared according to any method known to the art for the manufacture of pharmaceutical compositions and such compositions contain one or more agents from the group consisting of sweetening agents, flavouring agents, colouring agents and preserving agents in order to provide pharmaceutically elegant and palatable preparations.

Tablets contain the active ingredient in admixture with the non-toxic pharmaceutically acceptable excipients which are suitable for the manufacture of tablets. The excipients may be for example, inert diluents, such as calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be coated by known techniques to delay the disintegration and absorption in the gastrointestinal tract and thereby provide a sustained action over long period.

Formulations for oral use may also be presented as hard gelatin capsules wherein the active ingredients are mixed with an inert solid diluent, for example, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with the excipient suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum and gum acacia; dispersing or wefting agents may be a naturally-occurring phosphate, for example lecithin, or condensation products of an alkene oxide with fatty acids, for example polyoxyethylene stearate, or condensation products of ethylene oxide with long chain aliphatic alcohols, for example heptadecathyl-eneoxycetanol, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, P-hydroxybenzoate, one or more colouring agents, such as sucrose or saccharin. Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with the dispersing or wetting agent, suspending agent and one or more preservatives. Suitable dispersing or wetting agents and suspending agents are exemplified by those already mentioned above. Additional recipients, for example sweetening, flavouring and colouring agents, may also be present.

The pharmaceutical composition of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring phosphates, esters derived from fatty acids and hexitol anhydrides, for example sorbitan monooleate, and condensation products of the said partial esters with ethylene oxide, for example polyoxyethylene sorbitan monooleate. The emulsion may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solutions and isotonic sodium chloride solution. In addition, fixed oils are conventionally employed as a solvent or suspending medium. For this purpose any bland fixed oil may be employed including synthetic mono- or diglycerides. In addition, fatty acids such as oleic acid find use in the preparation of injectables.

Parenteral administration is generally characterized by injection, either subcutaneously, intramuscularly or intravenously. Injectables can be prepared in conventional forms, either as liquid solutions or suspension in liquid prior to injection, or as emulsions. Suitable excipients are for example, water, saline, dextrose, glycerol, ethanol or the like. In addition, if desired, the pharmaceutical compositions to be administered may also contain minor amounts of non-toxic auxiliary substance such as wetting or emulsifying agents, pH buffering agents and the like, such as for example, sodium acetate, sorbitan monolaurate, triethanolamine oleate, etc.

The amount of active ingredient that may be combined with the carrier materials to produce a single dosage form will vary depending upon the host treated and the particular mode of administration of humans may contain from 0.5 mg to 5 gm of active agent compounded with an appropriate and convent amount of carrier material which may vary from about 5 to about 95% of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, drug combination and the severity of the particular disease undergoing therapy.

The invention is further described and illustrated in the following specific examples.

Example 1

A. Preparation of Amidines, Compounds of Formula III

Selected amidines were from commercial sources (Aldrich and/or Lancaster). Those which were not commercially available were prepared according to published procedures. [Sandler, S. R. and Karo, W. in Organic Functional Group Preparations, 2nd Ed., Academic Press, Inc., Toronto, Volume II, Chapter 7, 1986 and Volume IIll, Chapter 6, 1989 and references cited therein; MacLeod, A. M. et al. in J. Med. Chem. 1990, 33, 2052–2059].

B. Preparation of 2-(3-Chlorophenyl)-2-(tetrahydropyran-2-yloxy)acetamidine hydrochloride To a solution of sodium bisulfite (27.66 g, 0.266 mol) in water (120 mL) was added 3-chlorobenzaldehyde (25.0 g, 0.178 mol). After stirring for 20 min, a solution of sodium cyanide (12.4 g, 0.2525 mol) in water (80 mL) was added dropwise. Ethyl acetate (50 mL) was added and the resulting mixture was stirred for another 3 h. The organic layer was collected, washed with brine, dried (sodium sulfate), filtered and evaporated to dryness. The residue was dissolved in dichloromethane (200 mL) and cooled in ice. Dihydropyran (20.62 g, 0.2451 mol) and pyridinium p-toluene sulfonate (6.5 g, 25.9 mmol) were then added successively and the mixture was stirred at room temperature for 16 h. The organic layer was successively washed with water (50 mL), 5% sodium bisulfite solution (2×50 mL) and brine (50 mL). The organic fraction was dried (sodium sulfate), filtered and evaporated to give an oil. Purification by column chromatography on silica gel using a mixture of hexane and ethyl acetate (95/5) as eluant afforded 31.5 9 (70%) of 2-(3-chlorophenyl)-2-[(tetrahydropyran-2-yloxy)]acetonitrile (mixture of diastereoisomers) as a clear oil which was contaminated with <5% of 3-chlorobenzaldehyde. $^1$H-NMR (CDCl$_3$) δ7.30–7.60 (m, 4H, Ar—H), 5.59 (s, 0.3H, αH) and 5.41 (s, 0.7H, αH), 5.12 (t, J=2.9 Hz, 0.3H, OCHO) and 4.77 (t, J=2.9 Hz, 0.7H, OCHO), 3.60–4.05 (m, 2H, CH$_2$O), 1.50–2.06 (m, 6H, 3 CH$_2$). Small pieces of sodium (192 mg, 7.9 mmol) was added to anhydrous ethanol (200 mL) under a positive pressure of nitrogen at room temperature. After all the sodium had dissolved, 2-(3-chlorophenyl)-2-[(tetrahydropyran-2-yloxy)]acetonitrile (19.54 g, 77.6 mmol) was added neat and the contents of the flask was rinsed with ethanol (20 mL) and added to the reaction mixture. The progress of the reaction can be monitored by TLC using a mixture of hexane and ethyl acetate (1/1) as solvent system. After stirring for 16 h, the reaction mixture was cooled to ca. −40° C. (dry ice-methanol-water) and an ethanolic solution of ammonia (77.6 mL of a 2M solution, 0.1552 mol) was quickly added followed by solid ammonium chloride (4.02 g, 75.15 mmol). The reaction mixture was allowed to warm to room temperature overnight. The reaction mixture was filtered over a pad of celite. The filtrate was collected and evaporated to dryness and then pumped under high vacuum to afford 2-(3-chlorophenyl)-2-(tetrahydropyran-2-yloxy)acetamidine hydrochloride (23 g) as a white foam in almost quantitative yield. $^1$H-NMR (CDCl$_3$) δ9.00–9.80 (br., 1H, NH), 8.00–8.80 (br., 1H, NH), 7.30–7.64 (m, 3H, Ar—H), 5.85 (s, 0.4H, αH) and 5.75 (s, 0.6H, αH), 4.84 (t, J=3.3 Hz, 0.4H, OCHO) and 4.57 (t, J=3.3 Hz, 0.6H, OCHO), 3.41–3.83 (m, 2H, CH$_2$O), 2.20–2.60 (br., 1H, NH), 1.46–1.86 (m, 6H, 3 CH$_2$).

C. In a similar manner, 2-pyridyl-2-(tetrahydropyran-2-yloxy)acetamidine hydrochloride salt was prepared as an orange foam (crude yield 96.0%). $^1$H-NMR (CDCl$_3$) δ9.00–9.80 (br., 1H, NH), 8.00–8.80 (br., 1H, NH), 8.56–8.61 (d, J=4.4 Hz, 1H, Py-H), 7.28–7.84 (m, 3H), 5.75 (s, 0.4H, αH) and 5.67 (s, 0.6H, αH), 4.93 (t, J=2.5 Hz, 0.4H, OCHO) and 4.71 (t, J=2.5 Hz, 0.6H, OCHO), 3.49–3.93 (m, 2H, CH$_2$O), 1.53–1.92 (m, 6H, 3 CH$_2$).

Example 2

A. Preparation of 5-Chloro-3-methoxy-[1,2,4]thiadiazole

To an ice-cooled mixture of O-methylisourea hydrochloride (11.06 g, 0.1 mol) in chloroform (150 mL) was added a solution of perchloromethyl mercaptan (11.0 mL, 0.1 mol) in chloroform (50 mL) dropwise over a period of 45 min. Then, a cold solution of sodium hydroxide (16 g, 0.4 mol in 30 ml water) was added dropwise while maintaining the reaction temperature to <5° C. The progress of the reaction was monitored by TLC using a mixture of hexane and ethyl acetate (9/1) as eluent. After 3 h at room temperature, the organic layer was collected, dried (sodium sulfate), filtered and then concentrated in vacuo. Purification by column chromatography on silica gel using a solvent gradient of a mixture of hexane and ethyl acetate (100/0, 95/5 then 9/1) afforded 5-chloro-3-methoxy-[1,2,4]thiadiazole (6.01 g, 39.9%) as a light yellow oil. $^1$H-NMR (CDCl$_3$) δ4.02 (s, OMe, 3H); $^{13}$C-NMR (CDCl$_3$) δ173.56 (C3), 169.68 (C5), 57.07 (OMe); MS (APCl) m/z 151.1 (M$_+$+1), 108.0, 94.0, 73.0, 58.0.

B. In a similar fashion, the following Compounds Were Prepared

3-Butoxy-5-chloro-[1,2,4]thiadiazole, light yellow oil, yield (50.9%). $^1$H-NMR (CDCl$_3$) δ4.35 (t, J=6.6 Hz, 2H, CH$_2$), 1.75 (m, 2H,CH$_2$), 1.44 (m, 2H, CH $_2$), 0.93 (t, J=7.1 Hz, 3H, CH$_3$); $^{13}$C-NMR (CDCl$_3$) d 173.27 (C3), 169.37 (C5), 70.17 (C1'), 30.70 (C2'), 18.96 (C3'), 13.67 (C4').

N-(5-Chloro-[1,2,4]thiadiazol-3-yl)-acetamide or 3-acetamido-5-chloro-1,2,4-thiadiazole, light yellow solid on standing, yield (34.8%). $^1$H-NMR (CDCl$_3$) δ2.50 (s, Me); $^{13}$C-NMR (CDCl$_3$) δ173.97 (C3), 171.86 (CO), 164.07 (C5), 22.54 (CH$_3$).

3-(5-Chloro-[1,2,4]thiadiazol-3-ylmethyl)-1H-indole or 5-chloro-3-{1H-indol-3yl-methyl}-1,2,4-thiadiazole, light brown solid, yield (28%). $^1$H-NMR (CDCl$_3$) δ8.29 (br. s, 1H, NH), 7.68 (d, J=7.8 Hz, 1H, CHNH), 7.11–7.33 (m, 4H, Ar—H), 4.48 (s, 2H, CH$_2$); $^{13}$C-NMR (CDCl$_3$) δ175.50 (C3), 173.00 (C5), 136.31, 127.13, 123.19, 122.26, 119.70, 119.05, 111.41, 110.55, 29.97 (CH$_2$); MS m/z 249.7 (M$^+$), 130.1, 117.1.

Example 3

A. Preparation of 5-Chloro-3-[3-chlorophenyl-1-(tetrahydropyran-2-yloxy) methyl]-[1,2,4]thiadiazole To an ice-cooled solution of 2-(3-chlorophenyl)-2-(tetrahydropyran-2-yloxy)acetamidine hydrochloride (12.0 g, 39.51 mmol) in dichloromethane (20 mL) and sodium hydroxide (9.49 g, 0.237 mol, dissolved in 60 mL water) was added a solution of perchloromethyl mercaptan (9.18 g, 49.46 mmol) in dichloromethane (50 mL) over a period of 35 min. The reaction mixture was stirred at ice-cold temperature for a further 1 h and the organic layer was collected, dried (sodium sulfate), filtered and concentrated in vacuo. Purification by column chromatography on silica gel using a mixture of hexane and ethyl acetate (94/6) afforded the title compound as a light yellow oil (8.4 g, 61.5%). $^1$H-NMR (CDCl$_3$) δ7.56 (d, J=6.9 Hz, 1H, Ar—H), 7.39–7.44 (m, 1H, Ar—H), 7.28–7.32 (m, 2H, Ar—H),6.08 and 6.03 (s, 0.5H each, α-H), 4.84 and 4.72 (t, J=3.1Hz, 0.5H each, OCHO), 3.49–3.92 (m, 2H, OCH$_2$), 1.55–1.94 (m, 6H, 3CH$_2$).

B. In a similar manner, the following Compounds Were Prepared

3-[(5-Chloro-[1,2,4]thiadiazol-3-yl)-(tetrahydropyran-2-yloxy)methyl]-pyridine, brown oil, 28.7% yield (mixture of diastereoisomers). $^1$H-NMR (CDCl$_3$) δ8.55 and 8.52 (d, J=4.5 Hz, 0.67 and 0.33 H each), 7.69–7.81 (m, 2H), 7.18–7.28 (m, 1H), 6.20 and 6.15 (s, 0.33 and 0.67 H each, ArCHO), 4.81–4.87 (m, 1H, OCHO), 3.84–3.90 (m, 1H, OCH), 3.44–3.54 (m, 1H, OCH), 1.90–1.96 (m, 1H), 1.75–1.80 (m, 2H), 1.51–1.60 (m, 3H); MS m/z 312.1 (M$^+$+1), 228, 210, 85.

5-Chloro-3-chloromethyl-[1,2,4]thiadiazole, brown oil, 83.6% yield. $^1$H-NMR (CDCl$_3$) δ4.70 (s); $^{13}$C-NMR (CDCl$_3$) δ174.33 (C3), 170.56 (C5), 40.17 (CH$_2$).

Example 4

A. Preparation of 1-{3-[phenyl-(tetrahydropyran-2-yloxy) methyl]-[1,2,4] thiadiazol-5-yl}-4-pyridin-2-yl-piperazine or 3-[1-phenyl-1-(tetrahydropyran -2-yloxy)methyl]-5-{4-[pyridin-2-yl]-piperazin-1 -yl}-1 ,2,4-thiadiazole To a solution of 3-[1-phenyl-1-(tetrahydropyran-2-yloxy) methyl]-5-chloro-[1,2,4]thiadiazole (3.11 g, 10 mmol) in DMF (50 mL) was added 1-(2-pyridyl)piperazine (3.26 g, 20 mmol) dissolved in DMF (5 mL) followed by triethylamine (4.04 g, 40 mmol). The resulting mixture was stirred at room temperature for 30 min then diluted with water (150 mL) and ethyl acetate (150 mL). The organic layer was collected, washed with water (100 mL), dried (sodium sulfate), filtered and concentrated in vacuo. Purification by column chromatography on silica gel using a solvent gradient of a mixture of hexane and ethyl acetate (7/3 and 1/1) afforded 1 -{3-[phenyl-(tetrahydropyran-2-yloxy) methyl]-[1,2,4] thiadiazol -5-yl}4-pyridin-2-yl-piperazine (4.31 g, 98.4%) as a colorless foam and as a mixture of diastereoisomers. $^1$H-NMR (CDCl$_3$) δ8.22 (d, J=4.6 Hz, 1H, Py-H), 7.51–7.58 (m, 3H), 7.27–7.39 (m, 3H), 6.68–6.71 (m, 2H), 5.93 and 5.88 (s, 0.5H each, αH), 4.91 and 4.67 (t, J=3.2 Hz, 0.5H each, OCHO), 3.51–4.02 (m, 2H, OCH$_2$), 3.69–3.71 (m, 4H, 2CH$_2$), 3.63–3.64 (m, 4H, 2CH$_2$), 1.51–1.97 (m, 6H, 3CH$_2$).

B. In a similar manner, the following Compounds Were Prepared

1 -{3-[3-Chlorophenyl-(tetrahydropyran-2-yloxy) methyl]-[1,2,4]thiadiazol-5-yl}-4-(pyridin-2-yl)-piperazine or 3-[1-[3-Chlorophenyl]-1 -(tetrahydropyran -2-yloxy) methyl}-5-{4-[pyridin-2-yl]-piperazin-1-yl}-1,2,4-thiadiazole. $^1$H-NMR (CDCl$_3$) δ (diastereoisomers) 8.22 (d, J=4.5 Hz, 1H, Py-H), 7.58–7.59 (m, 1H), 7.51–7.56 (m, 1H), 7.42–7.44 (m, 1H), 7.26–7.31 (m, 2H), 6.68–6.71 (m, 2H), 5.88 and 5.84 (s, 0.5H each, αH), 4.88 and 4.67 (t, 0.5H each, OCHO), 3.51–4.02 (m, 2H, OCH$_2$), 3.69–3.71 (m, 4H, 2CH$_2$), 3.64–3.65 (m, 4H, 2CH$_2$), 154–1.97 (m, 6H, 3CH$_2$).

1 -[Pyridin-2-yl]-4-{3-[pyridin-3-yl-(tetrahydropyran-2-ylbxy)methyl]-[1,2,4] thiadiazol-5-yl-piperazine, or 3-[1 -(pyridin-2-yl)-1 -(tetrahydropyran-2-yloxy) methyl]-5-{4-[pyridin-2-yl]-piperazin-1-yl}-1,2,4-thiadiazole light yellow solid, 75% yield. $^1$H-NMR (CDCl$_3$) δ8.58 (m, 1H), 8.22 (m, 1H), 7.62–7.75 (m, 2H), 7.43–7.51 (m, 1H), 7.13–7.18 (m, 1H), 6.62–6.68 (m, 2H), 6.00 and 5.98 (s, 0.5H each, αH), 4.93 and 4.74 (t, J=3.2 Hz, 0.5H each, OCHO), 3.40–4.05 (m, 2H, OCH$_2$), 3.63–3.65 (m, 4H, 2CH$_2$), 3.57–3.59 (m, 4H, 2CH$_2$), 1.48–1.97 (m, 6H, 3CH$_2$).

1-(3-Methoxy-[1,2,4]thiadiazol-5-yl)4-pyridin-2-yl-piperazine or 3-methoxy-5-{4-[pyridin-2-yl]-piperazin-1-yl}-1,2,4-thiadiazole, (54 % yield), white solid. Mp:144.3–144.8 ° C. $^1$H NMR: δ8.22 (s, 1H, Py-H), 7.54 (d, 2H), 6.71 (d, 2H), 4.00 (s, 3H, OMe), 3.72 (s, 4H, 2CH$_2$), 3.62 (s, 4H, 2CH$_2$).

1-(3-Phenyl-[1,2,4]thiadiazol-5-yl)4-pyridin-2-yl-piperazine or 3-phenyl-5-{4-[pyridin-2-yl]-piperazin-1-yl}-1,2,4-thiadiazole, (66 % yield), white solid. Mp:137.0–137.6° C. $^1$H NMR: δ8.25 (m, 3H), 7.55 (m, 1H), 7.45 (m, 3H), 6.72 (d, 2H), 3.75 (s, 8H, 4CH$_2$).

Example 5
Preparation of 3-[1-(2-pyridyl)piperazinyl-methyl]-5-[1-(2-pyridyl)piperazinyl]-[1,2,4] thiadiazole A solution of 1-(2-pyridyl)piperazine (6.75 mL, 44.4 mmol) in dichloromethane (10 mL) was added to a solution of 3-chloromethyl-5-chloro-[1,2,4]thiadiazole (1.5 g, 8.87 mmol) in DMF (20 mL) at 0° C. over a period of 30 min. Triethylamine (5 mL, 36 mmol) was added and the mixture was stirred at 0° C. for 30 min then at room temperature for 4 h. A voluminous white precipitate formed and dichloromethane (50 mL) was added and the resulting mixture was stirred at room temperature for another 16 h. The reaction mixture was quenched with water. The organic layer was collected, washed with brine, dried (sodium sulfate), filtered and concentrated in vacuo to a yellow solid. Purification by column chromatography on silica gel using a solvent mixture of 10% methanol in dichloromethane afforded 3-[1-(2-pyridyl)piperazinyl-methyl]-5-[1-(2-pyridyl)piperazinyl]-[1,2,4]thiadiazole (1.356 g, 36.3%). $^1$H NMR: δ8.23–8.25 (m, 1H), 8.19–8.21 (m, 1H), 7.53–7.57 (m, 1H), 7.46 –7.51 (m, 1H), 6.61–6.73 (m, 4H), 3.68–3.75 (m, 8H), 3.72 (s, 2H, C=CCH$_2$), 3.61–3.64 (m, 4H), 2.74–2.76 (m, 4H); MS (m/z): 423 (M$^+$+1), 380, 329, 303, 260, 235, 201, 176,147, 121.

Example 6
Preparation of 1-[1-(4-chlorophenyl)-1-phenylmethyl]-4-{3-[phenyl-(tetrahydropyran -2-yloxy)methyl]-[1,2,4] thiadiazol-5-yl}piperazine To a solution of 3-[1-phenyl-1-(tetrahydropyran-2-yloxy) methyl]-5-chloro-[1,2,4] thiadiazole (1.56 g, 5.02 mmol) in DMF (25 mL) was added 1-(4-chlorobenzhydryl) piperazine (2.88 g, 10.04 mmol) followed by triethylamine (2.03 g, 20.08 mmol). The resulting mixture was stirred at room temperature for 2 days. Volatile materials were removed in vacuo and the residue was partitionned between dichloromethane and water. The organic layer was collected, dried (sodium sulfate), filtered and evaporated to dryness. The residue was purified by column chromatography on silica gel using a mixture of hexane and ethyl acetate (8/2) thereby affording 1-[(4-chlorophenyl)phenylmethyl]-4-{3-[phenyl-(tetrahydropyran-2-yloxy)methyl]-[1,2,4]thiadiazol-5-yl}-piperazine (1.90 g, 67%) as a white solid and as a mixture of diastereoisomers. $^1$H-NMR (CDCl$_3$) δ7.55 (d, J=7.8 Hz, 1H), 7.22–7.39 (m, 13H, Ar—H), 5.89 and 5.85 (s, 0.4H and 0.6H each, αH), 4.90 and 4.64 (t, J=3.2 Hz, 0.4H and 0.6H each, OCHO), 4.29 (m, 1H, CH-Ar), 3.60–4.05 (m, 1H, OCH$_2$), 3.50 (m, 5H, 2CH$_2$+1H, OCH$_2$), 2.49 (m, 4H, 2CH$_2$), 1.50–1.94 (m, 6H, 3CH$_2$).

Example 7
A. Preparation of Phenyl-[5-(4-pyridin-2-yl-piperazin-1-yl)-[1,2,4]thiadiazol-3-yl]-methanol or 3-(α-hydroxybenzyl)-5-(4-pyridin-2-yl-piperazin-1-yl)-[ 1,2,4] thiadiazole A solution of 1 -{3-[phenyl-(tetrahydropyran-2-yloxy) methyl]-[1,2,4]thiadiazol -5-yl}-4-pyridin-2-yl-piperazine (4.1 g, 9.37 mmol) in 3N HCl (38 mL) was stirred at room temperature for 15 min. The reaction mixture was diluted with ethyl acetate and basified with 3N sodium hydroxide solution (pH ca. 10). The organic layer was collected, washed with water, dried (sodium sulfate), filtered and concentrated in vacuo. The solid was suspended in cold acetone, stirred at room temperature for 1 h, and filtered thereby affording the title compound (3.19 g, 96.4%) as an off-white solid. M.p. foamed at 149° C. and melted at 159–161° C.; $^1$H-NMR (CDCl$_3$) δ8.22 (d, J=4.6 Hz, 1H, Py-H), 7.52–7.56 (m, 3H), 7.35–7.39 (m, 2H), 7.28–7.30 (m, 1H), 6.68–6.72 (m, 2H), 5.77 (s, 1H, aH), 3.82 (br. s, 1H, OH), 3.69–3.72 (m, 4H, 2CH$_2$), 3.63–3.64 (m, 4H, 2CH$_2$); MS (m/z) 354 (M$^+$+1), 336, 309, 242, 204, 162, 121.

B. In a similar manner, the following Compounds Were Prepared

3-Chlorophenyl-[5-(4-pyridin-2-yl-piperazin-1 -yl)-[1 ,2,4]thiadiazol-3-yl]-methanol or 3-(a-hyd roxy-3-chlorobenzyl)-5-(4-pyridin-2-yl-piperazin-1 -yl)-[1,2,4] thiadiazole; $^1$H-NMR (CDCl$_3$) δ8.22 (d, J=4.1Hz, 1H, Py-H), 7.52–7.56 (m, 2H), 7.41–7.43 (m, 1H), 7.25–7.31 (m, 2H), 6.68–6.73 (m, 2H), 5.73 (s, 1H, αH), 3.90 (br. s, 1H, OH), 3.72 (m, 4H, 2CH$_2$), 3.64 (m, 4H, 2CH$_2$). Pyridin-2-yl-[5-(4-pyridin-2-yl-piperazin-1 -yl)-[1,2,4]thiadiazol-3-yl]-methanol or 3-(α-hydroxypyrid-2-ylmethyl)-5-(4-pyridin-2-yl-piperazin-1 -yl)-[ 1,2,4]thiadiazole; light yellow solid, 97% yield. $^1$H-NMR (CDCl$_3$) δ8.61 (d, J=4.8 Hz, 1H, Py-H), 8.22 (dd, J=4.8, 1.4 Hz, 1H), 7.68–7.72 (m, 1H), 7.53–7.55 (m, 1H), 7.47 (d, J=7.9 Hz,1H), 7.23–7.28 (m, 1H), 6.68–6.72 (m, 2H), 5.85 and 5.87 (s, 0.5H each, αH), 5.14 and 5.12 (s, 0.5H each, OH), 3.72 (m, 4H, 2CH$_2$), 3.64 (m, 4H, 2CH$_2$).

3-(α-hydroxybenzyl)-5-(4-[1-phenyl-1 -(3-chlorophenyl) methyl]piperazin-1 -yl) -[1,2,4]-thiadiazole; white solid, 100% yield. $^1$H-NMR (CDCl$_3$) δ7.50 (m, 2H), 7.22–7.39 (m, 12H, Ar—H), 5.74 and 5.72 (s, 0.5H each, αH), 4.30 (s, 1H, CH—Ar), 3.66 and 3.64 (s, 0.5H each, OH), 3.52 (m, 4H, 2CH$_2$), 2.50 (m, 4H, 2CH$_2$).

Example 8
A. Preparation of 3-benzoyl-5-[1-(2-pyridyl)piperazin4-yl]-1,2,4-thiadiazole To an ice-cooled suspension of 3-(1-hydroxy-1-phenylmethyl)-5-[1-(2-pyridyl)piperazin-4-yl]-1,2,4-thiadiazole (0.625 g, 1.77 mmol) in acetone was added dropwise over a period of ca. 10 min a solution of chromium trioxide (0.15 g, 1.5 mmol) dissolved in water (12 mL) and conc. sulfuric acid (0.33 mL). The resulting mixture was allowed to warm to room temperature and stirred for 16 h. The reaction mixture was diluted with ethyl acetate (100 mL), then made basic (pH ca. 10) by the addition of 3N sodium hydroxide solution. The organic layer was collected, washed with water, dried (sodium sulfate), filtered and concentrated in vacuo. Purification by column chromatography on silica gel using a solvent gradient of a mixture of hexane and ethyl acetate (6/4 and 4/6) afforded the title compound (390 mg, 75.3%) as a light yellow solid. The starting material (101 mg, 16.2%) was also recovered. M.p. 109.5–111.0° C.; $^1$H-NMR (CDCl$_3$) δ8.23–8.26 (m, 3H), 7.50–7.63 (m, 4H), 6.73–6.74 (m, 2H), 3.79 (m, 8H, 4CH$_2$); MS m/z 352 (M$^+$+1), 309, 258, 232, 204,147, 121,104, 77.

B. In a similar fashion, the following compounds were prepared

Pyridin-2-yl-[5-(4-pyridin-2-yl-piperazin-1 -yl)-[1 ,2,4] thiadiazol-3-yl]-methan one, white solid, 31% yield. $^1$H-NMR (CDCl$_3$) δ8.81 (d, J=4.5 Hz, 1H), 8.53 (d, J=4.8

Hz, 1H), 7.18–8.25 (m, 4H), 6.68–6.74 (m, 2H), 3.36–3.69 (m, 4H, 2CH$_2$), 3.58–3.63 (m, 4H, 2CH$_2$).

(3-Chloro-phenyl)-[5-(4-pyrid in-2-yl-piperazin-1-yl)-[1,2,4]thiad iazol-3-yl]-m ethanone, light yellow solid, 67.3% yield. M.p. 152.0–153.0° C.; $^1$H-NMR (CDCl$_3$) δ8.24–8.26 (m, 2H), 8.14 (d, J=7.9 Hz, 1H), 7.54–7.61 (m, 2H), 7.45 (t, J=7.9 Hz, 1H), 6.72–6.75 (m, 2H), 3.78 (m, 8H, 4CH$_2$); MS m/z 386 (M$^+$+1) 343, 292,204,162,147,139, 121,101.

{5–1 -[(1 -phenyl-1 -(3-chlorophenyl)methyl)-piperazin-4-yl]-[1,2,4]thiadiazol -3-yl}-phenyl-methanone; white solid, 68.2% yield. $^1$H-NMR (CDCl$_3$) δ8.21–8.23 (m, 2H), 7.61 (t, J=6.9 Hz, 1H), 7.47–7.51 (m, 2H), 7.39–7.41 (m, 4H), 7.24–7.35 (m, 5H), 3.65 (m, 4H, 2CH$_2$), 2.56 (m, 4H, 2CH$_2$).

Example 9
A. Preparation of Acid Addition Salt of a Compound of Formula I

To an ice-cooled suspension of 3-(1-hydroxy-1-phenylmethyl)-5-[1-(2-pyridyl)piperazin4-yl]-1,2,4-thiadiazole (0.61 g, 1.73 mmol) in methanol (10 mL) was bubbled HCl gas for ca. 2 min as a light yellow solution resulted. The volume of the reaction mixture was reduced to ca. 2 mL by rotary evaporation and diethyl ether was added. The voluminous yellow precipitate of the hydrochloride salt was collected by filtration and dried at 50° C. under vacuum for 3 h (575 mg). Phenyl-[5-(4-pyridin-2-yl-piperazin-1-yl)-[1,2,4] thiadiazol-3-yl]-methanol hydrochloride salt, light yellow solid, 85.4% yield. $^1$H-NMR (MeOD) δ8.11–8.19 (m, 1H), 7.98–8.02 (d, J=6.3 Hz, 1H), 7.42–7.52 (m, 3H), 7.23–7.38 (m, 3H), 7.07–7.14 (m, 1H), 5.75 (s, 1H, αH), 3.92 (m, 4H, 2CH$_2$), 3.83 (m, 4H, 2CH$_2$).

B. In a similar manner, the following compounds was made 3-benzoyl-5-[1-(2-pyridyl)piperazin4-yl]-1,2,4-thiadiazole hydrochloride salt, white solid, 84.4% yield. $^1$H-NMR (MeOD) δ8.20–8.22 (m, 2H), 8.13–8.17 (t, J=8.4 Hz,1H), 8.04–8.05 (d, J=6.2 Hz,1H), 7.68–7.72 (t, J=7.3 Hz,1H), 7.54–7.57 (m, 2H), 7.48–7.51 (d, J=9.2 Hz, 1H), 7.09–7.12 (t, J=6.7 Hz, 1H), 4.02 (m, 8H, 2CH$_2$), 3.96 (m, 8H, 2CH$_2$).

Example 10
In Vitro Inhibition of Gastric Acid Secretion by Compounds of Formula I Acid secretion is measured indirectly by the accumulation of the weak base $^{14}$C-aminopyrine in the isolated murine gastric glands of mouse. The assay is performed in polypropylene eppendorf tubes containing 0.5 mL of resuspended mouse gastric glands. In addition, tubes contain the tested drug, acid secretagogues (e.g. histamine, di-butyryl cyclic AMP (cAMP), carbachol) and $^{14}$C-aminopyrine. Tubes are incubated for 60 min. at 37 ° C. and continuously rotated. The reaction is stopped by centrifugation of the gland suspension for five min. at 1500 g. Supernatant is aspirated leaving the pellet containing intact gastric glands. The pellet is washed extensively and digested overnight in 1 mL of Protosol (Amersham). After neutralisation with acetic acid and addition of scintillation fluid, the radioactivity is counted in a beta-counter (Beckman). The amount of radioactivity trapped in the pellet corresponds directly with the amount of acid being secreted. Each experimental point is done in triplicate. In each experiment, energy independent consumption was estimated with 0.1 mM of dinitrophenol and basal acid secretion in the absence of acid stimulants. These values were then subtracted from corresponding results in order to calculate basal or secretagogue stimulated acid secretion.

Mouse glands respond to a variety of conventional secretagogues and post-receptor mediators but not to gastrin. The maximum stimulation of acid secretion is achieved with 1 mM cAMP, 0.1 mM histamine, 0.1 mM IBMX, 10 μM carbachol, 10 μM forskolin, 10 μM calcium ionophore A23187, 1 μM thapsigarin. Each experiment is repeated a number of times and all results are expressed as a % of the maximum stimulation. For the purpose of comparing the relative potency of the compounds, each experiment contains positive controls using omeprazole for post-receptor/cAMP mediated responses and ranitidine which inhibits histamine mediated acid secretion.

Using the above procedure, the IC$_{50}$ value for these compounds were as follows:

| Compound Name | IC$_{50}$ (μM) |
| --- | --- |
| 3-phenyl--5-{4-[pyridin-2-yl]-piperazin-1-yl}-1,2,4-thiadiazole | 4 |
| 3-benzoyl-5-{4-[pyridin-2-yl]-piperazin-1-yl}-1,2,4-thiadiazole | 6 |
| 3-(3-chlorobenzoyl)-5-{4-[pyridin-2-yl]-piperazin-1-yl}-1,2,4-thiadiazole. | 25 |
| 3-methoxy-5-{4-[pyridin-2-yl]-piperazin-1-yl}-1,2,4-thiadiazole | 100 |
| 3-(1-hydroxy-1-phenylmethyl)-5-{4-[pyridin-2-yl]-piperazin-1-yl}-1,2,4-thiadiazole | 30 |
| 3-benzoyl-5-{4-[1-phenyl-1-(4-chlorophenyl)methyl] piperazin-1-yl}-1,2,4-thiadiazole | 50 |

Example 11
Gastric Secretion Study in Rat

The objective of the study was to establish the antisecretory effects of two experimental compounds compared to Omeprazole. Male Sprague-Dawley rats (110 to 140 g in weight) were ordered from Ace Animals, Inc., Boyertown Pa. and were randomized into nineteen groups. The Control animals were administered carboxymethylcellulose (CMC) as the treated groups were administered the test materials in a suspension of CMC. Two groups were allotted to a reference standard of Omeprazole and were administered doses of 2 and 8 mg/kg. The other 4 dose groups were allotted to the 2 experimental compounds at doses of 8 and 32 mg/kg.

All test materials were administered by oral gavage as this is the intended route in humans. Each animal was dosed using a stainless steel ball-tipped gavage needle attached to an appropriate size syringe. All doses administered were based on fasted body weights taken prior to the dosing.

Two hours post drug administration, the animals were anesthetized using a short acting general anesthetic (Methoxital Sodium). The midline incision was made and the gastric duodenal area exposed. A ligature of thread was placed around the pylorus and tied tightly. This ligature around the pylorus stimulates the production of gastric acid. The incision was closed post ligation and the animal was replaced in its cage without access of food or water.

All rats were euthanized 2 hours post pylorus ligation using an overdose of sodium pentobarbital. The esophagus was ligated and the intact stomach was removed and opened along the great curvature. Gastric contents were collected in a plastic cup and transferred to a 15 ml conical tube. The contents were centrifuged for approximately 10 minutes. The supernatant was decanted and the volume was measured to the nearest tenth of a milliliter. 1 ml of the gastric contents were pipetted into 4 ml of distilled water and titrated with 0.01 N sodium hydroxide to a pH of 7.0. The acidity was measured by titration and the total acid output calculated.

| Activity of tested compounds | | |
|---|---|---|
| Compound tested | Average total acid output (mEq of HCl) | Average total gastric contents (ml) |
| Control | 298 | 2.5 |
| Omeprazole (2 mg/kg) | 296 | 2.2 |
| Omeprazole (8 mg/kg) | 164 | 1.9 |
| 3-phenyl-5-{4-[pyridin-2-yl]-piperazin-1-yl}-1,2,4-thiadiazole (8 mg/kg) | 223 | 2.2 |
| 3-phenyl-5-{4-[pyridin-2-yl]-piperazin-1-yl}-1,2,4-thiadiazole (32 mg/kg) | 100 | 1.2 |
| 3-(3-chlorobenzoyl)-5-{4-[pyridin-2-yl]-piperazin-1-yl}-1,2,4-thiadiazole (8 mg/kg) | 159 | 1.9 |
| 3-(3-chlorobenzoyl)-5-{4-[pyridin-2-yl]-piperazin-1-yl}-1,2,4-thiadiazole (32 mg/kg) | 271 | 2.9 |

What is claimed is:

1. 3,5 disubstituted 1,2,4-thiadiazoles compounds corresponding to the general formula (I):

(I)

or pharmaceutically acceptable salts thereof, wherein:

$R^1$ is selected from:

(1) 2-pyrazinyl, 2-pyridyl, 3-pyridyl, 4-pyridyl, wherein the pyridyl ring is optionally substituted with amino, lower alkyl, halogen, hydroxy, lower alkoxy, lower alkoxycarbonyl or carboxy;

(2) a group of formula:

—CHR$^2$R$^3$ in which $R^2$ and $R^3$ are independently lower carboalkoxy, carboxamido, lower alkanoyl, aryl, the aryl ring being optionally substituted with amino, halo, lower dialkylamino, hydroxy, lower alkoxy or lower alkyl;

Y is selected from:

(1) lower alkoxy, lower cycloalkyoxy, lower arylalkoxy, the alkyl or aromatic ring being optionally substituted with 1 to 2 substituents selected from amino, alkoxy, hydroxy, halo, alkylamino or dialkylamino;

(2) lower alkyl, lower cycloalkyl, aryl, lower arylalkyl, lower arylalkenyl, the alkyl or aromatic ring being optionally substituted with 1 to 2 substituents selected from amino, alkoxy, hydroxy, halo, alkylamino or dialkylamino;

(3) lower alkoxycarbonyl or carbonyl;

(4) ketone of formula:

$$R^4-\overset{O}{\underset{\|}{C}}-$$

wherein $R^4$ is lower alkyl, lower cycloalkyl, aryl or lower arylalkyl, the alkyl or aromatic ring being optionally substituted with 1 to 2 substituents selected from amino, alkoxy, hydroxy, halo, alkylamino or dialkylamino;

(5) carbamoyl group of formula $$R^4-\overset{H}{\underset{|}{N}}-\overset{}{\underset{\|}{C}}-\\ \phantom{R^4-N-}O$$

with $R^4$ being as defined above;

(6) amino, lower alkylamino, lower dialkylamino, (7) amide of formula:

$$R^4-\overset{O}{\underset{\|}{C}}-\overset{}{\underset{H}{N}}-$$

with $R^4$ being as defined above;

(8) alcohol of formula:

$$R^4-\overset{OH}{\underset{H}{\overset{|}{C}}}-$$

with $R^4$ being as defined above;

(9) sulfone or formula:

$$R^4-\overset{O}{\underset{\underset{O}{\|}}{\overset{\|}{S}}}-$$

with $R^4$ being as defined above;

(10) sulfoxide of formula:

$$R^4-\overset{}{\underset{\|}{S}}-\\ \phantom{R^4-}O$$

with $R^4$ being as defined above;

(11) sulfonamide of formnula:

$$R^4-\overset{O}{\underset{\underset{O}{\|}}{\overset{\|}{S}}}-\overset{}{\underset{H}{N}}-$$

with $R^4$ being as defined above;

(12) lower alkylthio, lower arylalkylthio, arylthio;

(13)

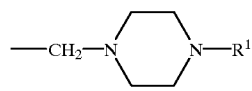

with R¹ being as defined above.

2. Compounds according to claim 1 wherein R¹ is 2-pyridyl:

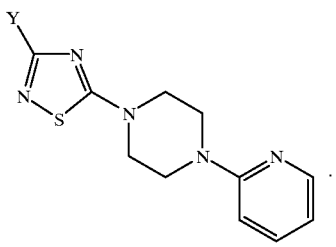

3. A compound according to claim 2 wherein Y is methyl which is 3-methyl-5-{4-[pyridin-2-yl]-piperazin-1 -yl}-1,2, 4-thiadiazole.

4. A compound according to claim 2 wherein Y is phenyl which is 3-phenyl-5-{4-[pyridin-2-yl]-piperazin-1 -yl}-1,2, 4-thiadiazole.

5. A compound according to claim 2 wherein Y is methoxy which is 3-methoxy-5-{4-[pyridin-2-yl]-piperazin-1-yl}-1 ,2 ,4-thiadiazole.

6. A compound according to claim 2 wherein Y is benzoyl which is 3-benzoyl-5-{4-[pyridin-2-yl]-piperazin-1 -yl}-1, 2,4-thiadiazole.

7. A compound according to claim 2 wherein Y is Ph-CH (OH)- which is 3-[1-phenyl- 1 -(hydroxy)methyl]-5-{4-[pyridin-2-yl]-piperazin-1 -yl}-1 ,2,4-thiadiazole.

8. A compound according to claim 2 wherein Y is 1-(3-chlorophenyl)-1-(hydroxy)methyl which is 3-{[1-[3-chlorophenyl]-1-(hydroxy)methyl}-5-{4-[pyridin-2-yl]-piperazin-1 -yl}-1 ,2,4-thiadiazole.

9. A compound according to claim 2 wherein Y is 3-chlorobenzoyl which is 3-(3-chlorobenzoyl)-5-4-[pyridin-2-yl]-piperazin-1 -yl}-1 ,2 ,4-thiadiazole.

10. A compound according to claim 2 wherein Y is 1-hydroxy-1-phenylmethyl which is 3-(1-hydroxy-1-phenylmethyl)-5-[1-(2-pyridyl)piperazin-4-yl]-1 ,2,4-thiadiazole.

11. Compounds according to claim 1 wherein R¹ is 1-(4-chlorophenyl)-1-phenylmethyl.

12. A compound according to claim 11 wherein Y is a-hydroxybenzyl, which is3-(α-hydroxybenzyl)-5-(4-[1-phenyl-1 -(4-chlorophenyl)methyl]piperazin-1-yl)-[1 ,2,4]-thiadiazole.

13. A compound according to claim 11 wherein Y is benzoyl which is 3-benzoyl-5-(4-[1 -phenyl-1 -(4-chlorophenyl)methyl]piperazin-1 -yl)-[1,2,4]-thiadiazole.

14. 2-Pyridinyl{5-[4-(2-pyridinyl)-1-piperazinyl]-1,2,4-thiadiazol-3-yl} methanone.

15. 3-{(4-Pyridin-2-yl-piperazin-1-yl)-methyl}-5-[1-(2-pyridyl)piperazin-4-yl]-1,2,4-thiadiazole.

16. A pharmaceutical composition comprising a compound according to claim 4 or a pharmaceutically acceptable salt thereof together with a pharmaceutically acceptable diluent or carrier thereof.

17. A pharmaceutical composition comprising a compound according to claim 6 or a pharmaceutically acceptable salt thereof together with a pharmaceutically acceptable diluent or carrier thereof.

18. A pharmaceutical composition comprising a compound according to claim 9 or a pharmaceutically acceptable salt thereof together with a pharmaceutically acceptable diluent or carrier thereof.

19. A method of treating peptic ulcers in animals which comprises administering an effective amount of a compound according to claim 4, in association with a pharmaceutically acceptable carrier.

20. A method of treating peptic ulcers in animals which comprises administering an effective amount of a compound according to claim 6, in association with a pharmaceutically acceptable carrier.

21. A method of treating peptic ulcers in animals which comprises administering an effective amount of a compound according to claim 9, in association with a pharmaceutically acceptable carrier.

* * * * *